(12) United States Patent
Clark et al.

(10) Patent No.: US 6,734,299 B1
(45) Date of Patent: *May 11, 2004

(54) TREATMENT FOR SUBSTRATES

(75) Inventors: Judith Mary Clark, Nottingham (GB); Andrew Hopkinson, Wirral (GB); Christopher Clarkson Jones, Wirral (GB); Ezat Khoshdel, Wirral (GB)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/409,169

(22) Filed: Sep. 30, 1999

(30) Foreign Application Priority Data

Sep. 30, 1998 (GB) .............................. 9821217

(51) Int. Cl.$^7$ .......................... C07H 13/00; C11D 3/37
(52) U.S. Cl. ..................... 536/123.1; 536/56; 510/470; 510/471; 510/473
(58) Field of Search ................. 510/471, 513, 510/515, 470, 473; 424/401; 536/56, 123.1

(56) References Cited

U.S. PATENT DOCUMENTS 6,248,710 B1 * 6/2001 Bijsterbosch et al. ....... 510/470
6,288,022 B1 * 9/2001 Clark ........................ 514/70
6,475,980 B2 * 11/2002 Bijsterbosch et al. ....... 510/473
6,506,220 B2 * 1/2003 Clark et al. ................ 8/115.51

FOREIGN PATENT DOCUMENTS

| EP | 0 514 588 | 11/1991 |
| GB | 1 470 234 | 4/1977 |
| WO | 95/00614 | 1/1995 |
| WO | 99/14295 | 3/1999 |
| WO | 99/36469 | 7/1999 |

* cited by examiner

Primary Examiner—James O. Wilson
Assistant Examiner—Ganapathy Krishnan
(74) Attorney, Agent, or Firm—Alan A. Bornstein

(57) ABSTRACT

A water-soluble or water-dispersible material for deposition onto a substrate during a treatment process, the material comprising:

(i) a deposition enhancing part having a polymeric backbone; and (ii) a benefit agent attached to the deposition enhancing part by a hydrolytically stable bond;

The material undergoes during the treatment process, a chemical change which does not involve the hydrolytically stable bond and by which change the affinity of the material onto the substrate is increased.

13 Claims, No Drawings

TREATMENT FOR SUBSTRATES

TECHNICAL FIELD

The present invention relates to a material comprising a benefit agent and a deposition aid for deposition of the benefit agent onto a substrate. It further relates to a method of depositing a benefit agent from solution or dispersion, onto a substrate.

BACKGROUND OF THE INVENTION

The deposition of a benefit agent onto a substrate, such as a fabric, is well known in the art. In laundry applications typical "benefit agents" include fabric softeners and conditioners, soil release polymers, sunscreens; and the like. Deposition of a benefit agent is used, for example, in fabric treatment processes such as fabric softening to impart desirable properties to the fabric substrate.

Conventionally the deposition of the benefit agent may rely upon the attractive forces between the oppositely charged substrate and the benefit agent. Typically this requires the addition of benefit agents during the rinsing step of a treatment process so as to avoid adverse effects from other charged chemical species present in the treatment compositions. For example, cationic fabric conditioners are incompatible with anionic surfactants in laundry washing compositions.

Such adverse charge considerations can place severe limitations upon the inclusion of benefit agents in compositions where an active component thereof is of an opposite charge to that of the benefit agent. For example, cotton is negatively charged and thus requires a positively charged benefit agent in order for the benefit agent to be substantive to the cotton, i.e. to have an affinity for the cotton so as to absorb onto it. Often the substantivity of the benefit agent is reduced and/or the deposition rate of the material is reduced because of the presence of incompatible charged species in the compositions.

The deterging nature of laundry wash compositions also places severe limitations upon the inclusion of neutral but hydrophobic or oily benefit agents which are not effectively deposited in the presence of surfactant.

Alternatively, when deposition of a conventional benefit agent is effected by mechanisms that do not rely upon charge interaction but upon other non-covalent forces, for example soil release polymers, other problems may occur, namely where interaction of an anionic surfactant with the benefit agent can also make the material so negatively charged and/or soluble as to overcome the other attractive interactions.

Furthermore, there is frequently another complication in achieving optimum deposition of a benefit agent onto a substrate, in that, the need for solubility of the benefit agent in the medium used to treat the substrate is in principle, incompatible with the requirement for the benefit agent to deposit/adsorb onto the substrate.

The present invention is directed towards materials for solving one or more of the above problems.

WO-A-98/00500 discloses detergent compositions comprising a peptide or protein deposition aid having a high affinity for fibres or a surface, and a benefit agent attached/adsorbed to the deposition aid. However, this deposition aid does not change chemically such as to increase its affinity for the substrate during the treatment process.

The present invention relates to materials for achieving initial solubility or dispersibility in the medium used to treat the substrate and effective deposition of one or more benefit-endowing groups thereon.

GB-A-1 031 484 discloses stable aqueous dispersions of elastic copolymers which can be converted to cross-linked polymers by the action of heat or acid. They can be used to produce films or covering layers. However, none of the compounds has a benefit agent attached to the deposition enhancing part. There is no disclosure of using these materials in methods of laundry or fabric care.

U.S. Pat. No. 5,730,760 discloses a process of fabric washing in which a dye redeposition inhibiting agent is used. The dye redeposition inhibiting polymer used is of a specific type, being produced by polymerising, for example, vinylester monomers. There is not any mention of materials having any surface substantive properties nor is there a description of any reaction by which such surface substantive properties increase during use.

WO-A-92/13114 discloses hair fixative polymers which form a film after application. The polymers are fundamentally different from those of the present invention in that they do not comprise a deposition part attached to a benefit agent. The polymeric material has no particular affinity for hair—it is just applied onto it. There is certainly no mention of a reaction which increases the affinity. Any reaction which occurs leads to the cross-linking of polymer and the formation of film. It is not disclosed that the polymers should be water-soluble of dispersible—they are normally dissolved in an inert carrier such as alcohol.

WO-A-95/35087 discloses a hair fixative amphoteric polymer composition. It is insoluble in water but can be solubilised by use of neutralisers or solubilising alcohol/water mixtures. The polymers do not to undergo any reaction which increases their affinity for hair. There is no benefit agent attached to the polymer.

WO-A-98/29528 discloses cellulose ethers in which some substituents are (poly)alkoxylated, analogues of the latter in which the (poly)alkoxylated groups are terminated with a cationic moiety in the form of a quaternary ammonium group, and cellulose ethers in which some substituents are carboxylic acids in the salt form (i.e. the materials are essentially carboxymethylcellulose variants). None of these substituents in any variant is of a kind which would undergo a chemical change to enhance fabric affinity.

WO-A-99/14245 discloses laundry detergent compositions containing cellulosic based polymers to provide appearance and integrity benefits to fabrics. These polymers are cellulosic polymers in which the saccharide rings have pendant oxygen atoms to which substituents 'R' are bonded, i.e. they are attached to the rings via an ether linkage. The groups 'R' can be hydrogen, lower alkyl or alkylene linkages terminated by carboxylic acid, ester or amide groups. Optionally, up to five alkyleneoxy groups may be interspersed between the groups are the respective oxygen atom. None of the pendant groups is a benefit agent group. However, at least some of these groups may undergo a chemical change such as hydrolysis, in the wash liquor. However no such change would result in an increased affinity for the fabric. On the contrary, because the "ester" group is configured with the carbonyl group closer to the polysaccharide than the oxygen atom (i.e. esters of carboxyalkyl groups), any hydrolysis will result in free acid substituents which will actually result in an increase in solubility and therefore, a decrease in affinity for the fabric.

WO-A-99/14295 discloses structures analogous to those described in WO-A-99/14245 but in one alternative, the substituents 'R' together with the oxygen on the saccharide ring, constitute pendant half-esters of certain dicarboxylic acids. A single example of such a material is given. Again, no pendant group is a benefit agent group. However, the dicarboxylic acid half-esters would tend to hydrolyse in the wash liquor and thereby increase affinity of the material for a cotton fabric. However, first, this mechanism of action or behaviour is not mentioned. Second, the hydrolysis rate of such dicarboxylic acids half esters is not as great as that of esters of monocarboxylic acids (which are not disclosed or claimed in WO-A-99/14295). Third, the degree of substitution for this variant is specified as being from 0.001 to 0.1. This is so low as to make the enhancement of fabric affinity too low to be worthwhile for this mechanism of action. Fourth, the structures described and claimed insofar as they have such half ester substituents, must also have substituents of the type which are carboxyalkyl groups or esters thereof, i.e. of the type also described in WO-A-99/14245. In the latter (ester) case, these would hydrolyse to the free acid form. The degree of substitution of the latter (0.2 to 2) is considerably higher than for the half-ester groups and the resultant increase in solubility would easily negate any enhanced affinity for the fabric by hydrolysis of the half-ester groups.

DEFINITION OF THE INVENTION

Accordingly, a first aspect of the present invention provides a water-soluble or water-dispersible material for deposition onto a substrate during a treatment process, wherein the material comprises:

(i) a deposition enhancing part having a polymeric backbone; and (ii) a benefit agent group attached to the deposition enhancing part by a hydrolytically stable bond;

such that the material undergoes during the treatment process, a chemical change which does not involve the hydrolytically stable bond and by which change the affinity of the material onto the substrate is increased.

A second aspect of the present invention also provides a method of depositing a benefit agent onto a substrate by its incorporation in a material according to the first aspect of the invention and applying said material to the substrate.

A third aspect of the present invention also provides compositions comprising a material according to the first aspect of the present invention. In particular, such compositions preferably comprise one or more surfactants and are suitable for use in washing applications such as laundry, personal washing, hand and machine dishwashing and household cleaning.

DETAILED DESCRIPTION OF THE INVENTION

The Material

The present invention requires the benefit agent group of the material to be attached to the deposition enhancing part by a hydrolytically stable bond. That means that the bonding of the benefit agent should be sufficiently stable so as not to undergo hydrolysis in the environment of the treatment process for the duration of that process. For example, in laundry cleaning applications, the material should be sufficiently stable so that the bond between the benefit and deposition enhancing part does not undergo hydrolysis in the wash liquor, at the wash temperature, before the benefit agent has been deposited onto the fabric.

Preferably, the bond between the benefit agent and the deposition enhancing part is such that the decay rate constant ($k_d$) of the material in an aqueous solution at 0.01 wt % of the material together with 0.1 wt % of anionic surfactant at a temperature of 40° C. at a pH of 10.5 is such that $k_d < 10^{-3} s^{-1}$.

The material of the present invention is water-soluble or water-dispersible in nature and comprises a deposition aid having a polymeric backbone and a benefit agent attached to the deposition aid by a hydrolytically stable bond.

By water-soluble, as used herein, what is meant is that the material forms an isotropic solution on addition to water or another aqueous solution.

By water-dispersible, as used herein, what is meant is that the material forms a finely divided suspension on addition to water or another aqueous solution.

By an increase in the affinity of the material for the fabric upon a chemical change, what is meant is that at some time during the treatment process, the amount of material that has been deposited is greater when the chemical change is occurring or has occurred, compared to when the chemical change has not occurred and is not occurring, or is occurring more slowly, the comparison being made with all conditions being equal except for that change in the conditions which is necessary to affect the rate of chemical change.

Deposition onto a substrate includes deposition by adsorption, co-crystallisation, entrapment and/or adhesion.

Deposition Enhancing Part

The deposition enhancing part has a polymeric backbone and is attached to the benefit agent group by means of a hydrolytically stable bond and in some cases, is that part of the material which undergoes a chemical change during treatment of a substrate which does not involve the hydrolytically stable bond with the benefit aid group. This chemical change results in an increase of the affinity of the material for the substrate and is referred to further below.

The polymeric backbone is chosen to have an affinity for the substrate onto which it is to be deposited. It is especially preferred that the polymeric backbone is of a similar chemical composition to the substrate onto which it is to be deposited.

For example, if the fabric is cellulosic in nature, e.g. cotton, the polymeric backbone is preferably cellulose or a cellulose derivative or a another β-1,4-linked polysaccharide having an affinity for cellulose, such as mannan and glucomannan.

The polysaccharide may be straight or branched. Many naturally occurring polysaccharides have at least some degree of branching, or at any rate, at least some saccharide rings are in the form of pendant side groups on a main polysaccharide backbone.

Other polymeric backbones suitable as according to the present invention include those described in Hydrocolloid Applications, A. Nussinswitch, Blackie 1997.

The chemical change which causes the increased fabric affinity may occur in any part or parts of the material, for example in the deposition enhancing part or in one or more benefit agent groups. Yet again, it may occur in a substituent group provided specifically for that purpose, attached to the deposition enhancing part or to one or more of the benefit agent groups. Such substituents may either be directly attached, or attached via a linking group.

Thus, for example, the polymeric backbone may incorporate a region or regions which undergo the chemical change to cause the increased affinity of the material for the substrate during the treatment process. However, it is preferred for the backbone to have attached thereto, one or more suitable groups (preferably so as to render the material either water-soluble or water-dispersible), the chemical change in which group(s) causes the increased substrate affinity.

The chemical change which causes the increased substrate affinity is preferably caused by hydrolysis, perhydrolysis or bond-cleavage, optionally catalysed by an enzyme or another catalyst. Hydrolysis of substituent ester-linked groups is typical. However, preferably this change is not merely protonation or deprotonation.

Most preferably, the chemical change occurs in or to a group covalently bonded to a polymeric backbone, especially, the loss of one or more such groups. In most cases, such group(s) is/are pendant on the backbone, e.g. being attached via an ester linkage.

By ester linkage is meant that the hydrogen of an —OH group has been replaced by a substituent such as R'—CO—, R'SO$_2$— etc to form a carboxylic acid ester, sulphonic acid ester (as appropriate) etc together with the remnant oxygen attached to the saccharide ring. In some cases, the group R' may for example contain a heteroatom, e.g. as an —NH— group attached to the carbonyl, sulphonyl etc group, so that the linkage as a whole could be regarded as a urethane etc linkage. However, the term ester linkage is still to be construed as encompassing these structures.

The average degree of substitution of these pendant groups which undergo the chemical charge is preferably from 0.1 to 3 (e.g. from 0.3 to 3), more preferably from 0.1 to 1 (e.g. from 0.3 to 1).

The polysaccharide may be straight or branched. Many naturally occurring polysaccharides have at least some degree of branching, or at any rate at least some saccharide rings are in the form of pendant side groups (which are therefore not in themselves counted in the degree of substitution) on a main polysaccharide backbone.

A polysaccharide comprises a plurality of saccharide rings which have pendant hydroxyl groups. The pendant groups can be bonded chemically or by other bonding mechanism, to these hydroxyl groups by any means described hereinbelow. The "average degree of substitution" means the average number of pendant groups per saccharide ring for the totality of polysaccharide molecules in the sample and is determined for all saccharide rings whether they form part of a linear backbone or are themselves, pendant side groups in the polysaccharide.

Preferred materials of the invention are cellulosic polymers of formula (I):

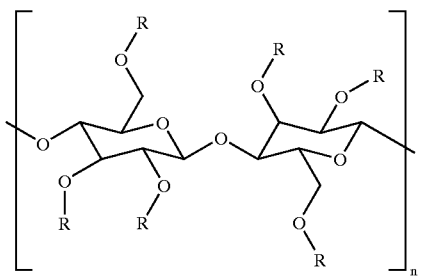

(I)

wherein at least one or more R groups of the polymer are independently selected benefit agent groups and at least one or more R groups are independently selected from groups of formulae:

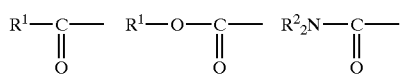

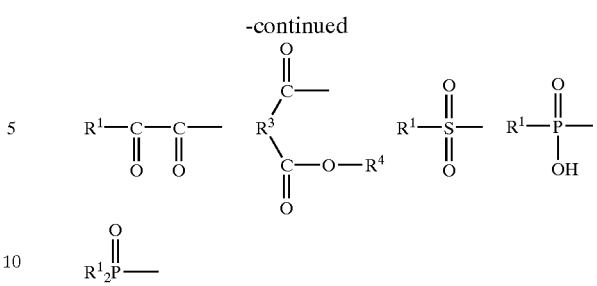

wherein each $R^1$ is independently selected from $C_{1-20}$ (preferably $C_{1-6}$) alkyl, $C_{2-20}$ (preferably $C_{2-6}$) alkenyl (e.g. vinyl) and $C_{5-7}$ aryl (e.g. phenyl) any of which is optionally substituted by one or more substituents independently selected from $C_{1-4}$ alkyl, $C_{1-12}$ (preferably $C_{1-4}$) alkoxy, hydroxyl, vinyl and phenyl groups;

each $R^2$ is independently selected from hydrogen and groups $R^1$ as hereinbefore defined;

$R^3$ is a bond or is selected from $C_{1-4}$ alkylene, $C_{2-4}$ alkenylene and $C_{5-7}$ arylene (e.g. phenylene) groups, the carbon atoms in any of these being optionally substituted by one or more substituents independently selected from $C_{1-12}$ (preferably $C_{1-4}$) alkoxy, vinyl, hydroxyl, halo and amine groups;

each $R^4$ is independently selected from hydrogen, counter cations such as alkali metal (preferably Na) or ½ Ca or ½ Mg, and groups $R^1$ as hereinbefore defined; and groups R which together with the oxygen atom forming the linkage to the respective saccharide ring forms an ester or hemi-ester group of a tricarboxylic- or higher polycarboxylic- or other complex acid such as citric acid, an amino acid, a synthetic amino acid analogue or a protein.

For the avoidance of doubt, as already mentioned, in formula (I), some of the R groups may optionally have one or more structures, for example as hereinbefore described. For example, one or more R groups may simply be hydrogen or an alkyl group.

Preferred groups which undergo the chemical change may for example be independently selected from one or more of acetate, propanoate, trifluroacetate, 2-(2-hydroxy-1-oxopropoxy) propanoate, lactate, glycolate, pyruvate, crotonate, isovalerate cinnamate, formate, salicylate, carbamate, methylcarbamate, benzoate, gluconate, methanesulphonate, toluene, sulphonate, groups and hemiester groups of fumaric, malonic, itaconic, oxalic, maleic, succinic, tartaric, aspartic, glutamic, and malic acids.

Particularly preferred such groups are the monoacetate, hemisuccinate, and 2-(2-hydroxy-1-oxopropoxy) propanoate. The term "monoacetate" is used herein to denote those acetates with the degree of substitution of 1 or less on a cellulose or other β-1,4 polysaccharide backbone.

Cellulose esters of hydroxyacids can be obtained using the acid anhydride in acetic acid solution at 20–30° C. and in any case below 50° C. When the product has dissolved the liquid is poured into water (b.p. 316,160). Tri-esters can be converted to secondary products as with the triacetate. Glycollic and lactic ester are most common.

Cellulose glycollate may also be obtained from cellulose chloracetate (GB-A-320 842) by treating 100 parts with 32 parts of NaOH in alcohol added in small portions.

An alternative method of preparing cellulose esters consists in the partial displacement of the acid radical in a cellulose ester by treatment with another acid of higher ionisation constant (FR-A-702 116). The ester is heated at about 100° with the acid which, preferably, should be a solvent for the ester. By this means cellulose acetate-oxalate, tartrate, maleate, pyruvate, salicylate and phenylglycollate have been obtained, and from cellulose tribenzoate a cellulose benzoate-pyruvate. A cellulose acetate-lactate or acetate-glycollate could be made in this way also. As an example cellulose acetate (10 g.) in dioxan (75 ml.) containing oxalic acid (10 g.) is heated at 100° for 2 hours under reflux.

Multiple esters are prepared by variations of this process. A simple ester of cellulose, e.g. the acetate, is dissolved in a mixture of two (or three) organic acids, each of which has an ionisation constant greater than that of acetic acid ($1.82 \times 10^{-5}$). With solid acids suitable solvents such as propionic acid, dioxan and ethylene dichloride are used. If a mixed cellulose ester is treated with an acid this should have an ionisation constant greater than that of either of the acids already in combination.

A cellulose acetate-lactate-pyruvate is prepared from cellulose acetate, 40 per cent. acetyl (100 g.), in a bath of 125 ml. pyruvic acid and 125 ml. of 85 per cent. lactic acid by heating at 100° for 18 hours. The product is soluble in water and is precipitated and washed with ether-acetone. M.p. 230–250°.

In the case of those materials having a cellulose backbone and pendant ester groups, without being bound by any particular theory or explanation, the inventors have conjectured that the mechanism of deposition is as follows.

Cellulose is substantially insoluble in water. Attachment of the ester groups to make a cellulose derivative causes disruption of the hydrogen bonding between rings of the cellulose chain or chains, thus increasing water solubility or dispersibility. In the treatment liquor, the ester groups are hydrolysed, causing the cellulose derivative to increase its affinity for the substrate, e.g. the fabric.

In the case when solubilising groups are attached to the polymeric backbone, this is typically via covalent bonding and, may be pendant upon the backbone or incorporated therein. The type of solubilising group may alter according to where the group is positioned with respect to the backbone.

The molecular weight of the deposition enhancing part may typically be in the range of 1,000 to 2,000,000, for example 10,000 to 1,500,000.

Benefit Agent Groups

The benefit agent groups may be selected from any groups which is used to impart desirable properties to the substrate upon which the material of the present invention is to be deposited. The benefit agent group may be, in particular, one which imparts a desirable property to a fabric, household surface, dish or cutlery surface, skin, hair, teeth or nail substrate, especially to a fabric substrate. In practice, a material according to the present invention may comprise two or more benefit agent groups on the same molecule, either of the same kind or of different kinds.

For hydrophobic benefit agents groups, the deposition enhancing part should be sufficiently soluble to either take the benefit agent group into solution so producing a water-soluble material, or to make the material water dispersible. For the colloidal benefit agents it is preferred that the deposition aid promotes the dispersal of the material.

The material of the present invention must comprise at least one deposition enhancing moiety and at least one benefit agent moiety. However, dependent upon the nature of each moiety, the weight ratio of deposition aid moiety to benefit agent moiety is preferably from 100:1 to 1:10,000, more preferably from 10:1 to 1:5,000 and most preferably from 5:1 to 1:500.

According to the benefit agent type(s), the material of the present invention may, for example be incorporated in liquid or solid fabric treatment compositions, laundry (wash) compositions, household cleaning compositions, hand and machine dishwashing compositions, or personal care compositions.

For fabrics substrates, for example in laundry applications, examples of suitable fabric care benefit agents include silicones, fabric softening clays, or L-beta phase surfactants.

It is especially preferred if the benefit agent gives a perceivable benefit to a fabric.

The present invention is of particular use when the composition is used in laundering fabrics and in this context a benefit agent can be defined as any agent which affects the feel, appearance, or the perception of a fabric. For this application, preferred benefit agent groups may be selected from the following:

(a) fabric softening and/or conditioning agents;

(b) lubricants for inhibition of fibre damage and/or for colour care and/or for crease reduction and/or for ease of ironing;

(c) UV absorbers such as fluorescers and photofading inhibitors, for example sunscreens/UV inhibitors and/or anti-oxidants;

(d) fungicides and/or insect repellents; and (e) perfumes.

Suitable fabric softening and/or conditioning agent groups are preferably chosen from those of the cationic detergent active type, clays and silicones. Those of the cationic detergent active type are preferably selected from quaternary ammonium cationic molecules, for example those having a solubility in water at pH 2.5 and 20° C. of less than 10 g/l.

It is preferred for the ester-linked quaternary ammonium compounds to contain two or more ester groups. In both monoester and the diester quaternary ammonium compounds it is preferred if the ester group(s) is a linking group between the nitrogen atom and an alkyl group. The ester groups(s) are preferably attached to the nitrogen atom via another hydrocarbyl group.

As used herein the term 'ester group', when used in the context of a group in the quaternary ammonium material, includes an ester group which is a linking group in the molecule.

Typical are quaternary ammonium compounds containing at least one ester group, preferably two, wherein at least one higher molecular weight group containing at least one ester group and two or three lower molecular weight groups are linked to a common nitrogen atom to produce a cation and wherein the electrically balancing anion is a halide, acetate or lower alkosulphate ion, such as chloride or methosulphate. The higher molecular weight substituent on the nitrogen is preferably a higher alkyl group, containing 12 to 28, preferably 12 to 22, e.g. 12 to 20 carbon atoms, such as coco-alkyl, tallowalkyl, hydrogenated tallowalkyl or substituted higher alkyl, and the lower molecular weight substituents are preferably lower alkyl of 1 to 4 carbon atoms, such as methyl or ethyl, or substituted lower alkyl. One or more of the said lower molecular weight substituents may include an aryl moiety or may be replaced by an aryl, such as benzyl, phenyl or other suitable substituents.

More preferably, the quaternary ammonium material comprises a compound having two long chain alkyl or alkenyl chains with an average chain length equal to or greater than $C_{14}$. Even more preferably each chain has an average chain length equal to or greater than $C_{16}$. Most preferably at least 50% of each long chain alkyl or alkenyl group has a chain length of $C_{18}$. It is preferred if the long chain alkyl or alkenyl groups are predominantly linear.

It is particularly advantageous if the cationic softening compound is a quaternary ammonium compound with two $C_{12}$–$C_{22}$ alkyl or alkenyl groups connected to a quaternary ammonium group via at least one ester link, preferably two ester links, or else a compound with a single long chain with an average chain length greater than or equal to $C_{20}$. Examples of cationic softeners are described in U.S. Pat. No. 4,137,180 and WO-A-93/23510.

The most preferred type of ester-linked quaternary ammonium material that can be used as benefit agent group(s) is represented by the formula (A):

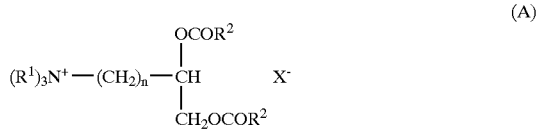

(A)

wherein $R^1$, n, $R^2$ and $X^-$ are as defined above.

It is advantageous for environmental reasons if the quaternary ammonium material is biologically degradable.

Preferred materials of this class such as 1,2 bis[hardened tallowoyloxy]-3-trimethylammonium propane chloride and their method of preparation are, for example, described in U.S. Pat. No. 4,137,180. Preferably these materials comprise small amounts of the corresponding monoester as described in U.S. Pat. No. 4,137,180 for example 1-hardened tallowoyloxy-2-hydroxy-3-trimethylammonium propane chloride.

Another class of preferred ester-linked quaternary ammonium materials for use as benefit agent group(s) can be represented by the formula:

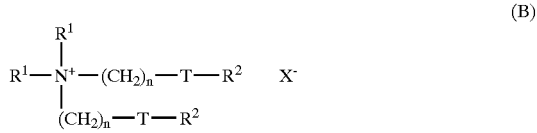

(B)

wherein each $R^1$ group is independently selected from $C_{1-4}$alkyl, hydroxyalkyl or $C_{2-4}$ alkenyl groups; and wherein each $R^2$ group is independently selected from $C_{8-28}$ alkyl or alkenyl groups; $X^-$ is any suitable counter-ion, i.e. a halide, acetate or lower alkosulphate ion, such as chloride or methosulphate.

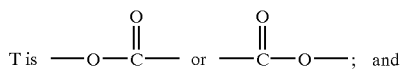

n is an integer from 1–5 or is 0

It is especially preferred that each $R^1$ group is methyl and each n is 2.

Of the compounds of formula (B), Di-(tallowyloxyethyl)-dimethyl ammonium chloride, available from Hoechst, is the most preferred. Di-(hardened tallowyloxyethyl)dimethyl ammonium chloride, ex Hoechst and di-(tallowyloxyethyl)-methyl hydroxyethyl methosulphate are also preferred.

Another preferred class of quaternary ammonium cationic fabric softening agent for use as the benefit agent group(s)is defined by formula (C):

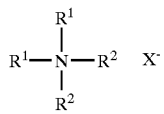

(C)

where $R^1$, $R^2$ and X are as hereinbefore defined.

A preferred material of formula (C) is di-hardened tallow-diethyl ammonium chloride, sold under the Trademark Arquad 2HT.

It is also possible to use certain mono-alkyl cationic surfactants which on their own can be used in main-wash compositions for fabrics. Cationic surfactants that may be used include quaternary ammonium salts of the general formula $R_1R_2R_3R4N^+ X^-$ wherein the R groups are long or short hydrocarbon chains, typically alkyl, hydroxyalkyl or ethoxylated alkyl groups, and X is a counter-ion (for example, compounds in which $R_1$ is a $C_8$–$C_{22}$ alkyl group, preferably a $C_8$–$C_{10}$ or $C_{12}$–$C_{14}$ alkyl group, $R_2$ is a methyl group, and $R_3$ and R4, which may be the same or different, are methyl or hydroxyethyl groups); and cationic esters (for example, choline esters).

If the fabric softening and/or conditioning group(s) is/are silicones, these may for example be selected from those disclosed in GB-A-1 549 180, EP-A-459 821 and EP-A-459 822. However, these silicones if used for other benefits listed under the class (b) above, can be regarded as "lubricants". Other suitable lubricants include any of those known for use as dye bath lubricants in the textile industry.

Suitable photofading inhibitors of the sunscreen/UV inhibitor type are preferably molecules with an extinction co-efficient greater than 2000 l $mol^{-1}$ $cm^{-1}$ at a wavelength of maximal absorption. Typically for a sunscreen maximal absorption occurs at wavelengths of 290–370 nm, more usually 310–350 nm, especially 330–350 nm.

Examples of suitable sunscreens are given in *Cosmetic Science and Technology Series*, Vol. 15; Sunscreens; 2nd edition; edited by Lowe, Shoath and Pathak; *Cosmetics and Toiletries*; Vol. 102; March 1987; pages 21–39; and *Evolution offModern Sunscreen Chemicals*; pages 3–35 both by N. A. Saarth.

In particular, suitable sunscreens include carboxylic acids or carboxylic acid derivatives, for example acrylates, cinnamates and benzoates or derivatives thereof, such as 4-methoxy cinnamate salicylates, PABA, 4-acetoxy benzoate dibenzoylmethanes, phenyl benzoimidazoles, aminobenzoates, benzotriazoles and benzophenones.

Suitable photofading inhibitors of the anti-oxidant type include benzofurans, coumeric acids or derivatives thereof, for example 2-carboxy benzofuran and bis(p-amine sulphonates) triazine, DABCO derivatives, tocopherol derivatives, tertiary amines and aromatic substituted alcohols eg butylated hydroxytoluene (BHT), Vitamin C (ascorbic acid) and vitamin E.

Suitable fungicides include 6-acetoxy-2,4-dimethyl-m-dioxane, diiodomethyl-p-tolysulphone, 4,4-dimethyloxaolidine, hexahydro-1,3,5-tris(2-hydroxyethyl)-s-triazine, sodium dimethyldithiocarbamate, sodium 2-mercaptobenzothioazole, zinc dimethyldithiocarbamate, zinc 2-mercaptobenzothiazole, sodium 2-pyridinethiol-1-oxide, sodium 2-pyridinethiol-1-oxide and N-trichloromethylthio-4-cyclohexene-1,2-dicarboximide.

Suitable insect repellents include N-alkyl neoalkanamides wherein the alkyl is of 1 to 4 carbon atoms and the neoalkanoyl moiety is of 7 to 14 carbon atoms preferably N-methyl neodecanamide; N,N-diethyl meta toluamide (DEET), 2-Hydroxyethyl-n-octyl sulphide (MGK 874); N-Octyl bicycloheptene dicarboximide (MGK 264); hexahydrodibenzofuran (MGK 11), Di-n-propyl isocinchomerate (MGK 326); 2-Ethyl-1,3-hexanediol, 2-(n-butyl)-2-ethyl-1,3-propanediol, dimethyl phthalate, dibutyl succinate, piperonyl butoxide, pyrethrum, Cornmint, Peppermint, American spearmint, Scotch spearmint, Lemon oil, Citronella, cedarwood oil, pine oil, Limonene, carvone, Eucalyptol, Linalool, Gum Camphor, terpineol and fencholic acid.

Suitable perfumes are commercially available and have an undisclosed molecular structure.

Suitable clays include a three layered smectite clay, preferably having a cation exchange capacity as described in GB1400898 (Procter and Gamble). Especially preferred are clays which are 2:1 layer phyllosilicates possessing a lattice charge deficiency in the range of 0.2 to 0.4 g equivalents per half unit cell as described in EP 0 350 288 (Unilever).

Latex materials are also defined as benefit agents. A latex is defined as a material suitable for improving the drape of fabric, suitable materials include a polyvinylacetate homopolymer such as 9802 (Vinamul).

Benefit agent may also include resins such as Knittex BE (Ciba-Geigy) or silicas such as Crosanaol NS (Crosfield), these Benefit Agents prevent pill formation on the fabric.

The benefit agent may be any material which is encapsulated. Suitable encapsulating materials include starches and poly(vinylacetate) and urea/formaldehyde condensate based materials.

Suitable materials that may be encapsulated include perfumes, insect repellents, fungicides, or photo protective agents.

The benefit agent is attached to the deposition enhancing part. This attachment may be by adsorption or by chemical bonding. If the Benefit Agent is adsorbed this is preferably by simple physisorption.

If the benefit agent is attached to the deposition enhancing part this may be via a linking agent. However, direct chemical bonding may also be used, as described in more detail hereinbelow.

Suitable linking agents are molecules which show a high affinity for the Benefit Agent. It is preferred if the linking agent is covalently attached to the backbone of the deposition enhancing part. It is also advantageous if the linking agent is covalently bound to the benefit agent.

Other Substituents

As well as the benefit agent groups and any pendant groups which undergo a chemical change to enhance deposition, pendant groups of other types may optionally be present, i.e. groups which do not confer a benefit and which do not undergo a chemical change to enhance substrate affinity. Within that class of other groups is the sub-class of groups for enhancing the solubility of the material (e.g. groups which are, or contain one or more free carboxylic acid/salt and/or sulphonic acid/salt and/or sulphate groups).

Examples of solubility enhancing substituents include carboxyl, sulphonyl, hydroxyl, (poly)ethyleneoxy- and/or (poly)propyleneoxy-containing groups, as well as amine groups.

The other pendant groups preferably comprise from 0% to 65%, more preferably from 0% to 10% of the total number of pendant groups. The water-solubilising groups could comprise from 0% to 100% of those other groups but preferably from 0% to 20%, more preferably from 0% to 10%, still more preferably from 0% to 5% of the total number of other pendant groups.

Synthetic Routes

There are basically two general methods for preparing a water-soluble or water dispersable material of the class comprising a deposition aid including or having attached thereto, group(s) which undergo the chemical change.

Method 1

First the deposition enhancement part is synthesised; and
then the benefit agent(s) is/are grafted onto the backbone of the deposition enhancement part.

Method 2

First the benefit agent is grafted onto the polymeric backbone of a precursor of the deposition enhancing part; and
then the precursor is converted into the desired deposition enhancing part.

For Methods 1 and 2 the general method for preparing the deposition enhancing part may be achieved by a number of different synthetic routes, for example:

(a) polymerisation of suitable monomers, for example, enzymatic polymerisation of saccharides, e.g. per S. Shoda, & S. Kobayashi, Makromol. Symp. 1995, 99, 179–184 or oligosaccharide synthesis by orthogonal glycosylation e.g. per H. Paulsen, Angew. Chem. Int. Ed. Engl. 1995, 34, 1432–1434;

(b) derivatisation of a polymeric backbone (either naturally occurring, especially polysaccharides, especially beta-1,4-linked polysaccharides, especially cellulose, mannan, glucomannan, galactomannan, xyloglucan; or synthetic polymers) up to the required degree of substitution with functional groups which improve the solubility of the polymer for deposition, using a reagent (especially acid halides, especially carboxylic acid halides, anhydrides, carboxylic acid anhydrides, carboxylic acids, carbonates) in a solvent which either dissolves the backbone, swells the backbone, or does not swell the backbone but dissolves or swells the product).

(c) hydrolysis of polymer derivatives (especially esters) down to the required degree of substitution; or (d) a combination of any two or more of routes (a)–(c).

Some materials which are suitable as the deposition-enhancing part may be commercially available.

The degree and pattern of substitution from routes (a) or (c) may be subsequently altered by partial removal of functional groups by hydrolysis or solvolysis or other cleavage. The relative proportions of reactants and reaction conditions may also be used to control the degree of substitution. In addition, or alternatively, the degree of polymerisation of the backbone may be reduced before, during, or after the derivatisation with functional groups. The degree of polymerisation of the backbone may be increased by further polymerisation or by cross linking agents before, during, or after the derivatisation step.

For Methods 1 and 2 the general method for grafting the benefit agent onto the deposition enhancement part can be effected either:

(i) by physical attraction between the delivery aid and the benefit agent, especially the use of a block copolymer where one block has a physical affinity for the benefit agent and the other block can undergo a chemical change during treatment which increases its affinity for the target substrate, or (ii) by grafting the benefit agent onto the polymeric backbone of the delivery aid using a bond which is relatively hydrolytically stable. For example, one could use an ester bond which is more stable than the one intended to undergo the chemical change but which is not be completely stable. For example a conjugated or aromatic ester. Such grafting can be accomplished by reacting the polymeric backbone or already-pre-modified polymeric backbone (especially cellulose esters, especially cellulose acetates) with a benefit-agent reagent (especially acid halides, especially carboxylic acid halides, anhydrides, carboxylic acid anhydrides, carboxylic acids, isocyanates, triazine derivatives, amines, hydrazines) in a solvent which dissolves the backbone or delivery aid, swells the backbone or delivery aid, or does not swell the backbone or delivery enhancing part (depending on whether grafting the benefit agent first or last) but dissolves or swells the product.

For the grafting, typically, radiation methods may be used, for example:

1. Grafting by Mutual Irradiation (The Direct Radiation Grafting of the Benefit Group Onto the Polymer Backbone).

The mutual irradiation method is the simplest radiation-chemical method for producing graft copolymers. The procedure involves the irradiation of a polymeric substrate in the presence of a benefit group-containing monomer solution, preferably in the absence of oxygen at around ambient temperature for a given time and irradiation dose. It is known that most radiation-initiated polymerization proceeds by free radical mechanisms, and that it is initiated by the free radicals arising from the radiolysis of the either polymer or monomer, although the mutual irradiation is the most efficient method of achieve grafting.

2. Grafting on to Radiation-Peroxided Polymer Backbone

In this method, the polymeric samples of (typically, a cellulosic) polymer backbone are first irradiated, typically in the presence of air or pure oxygen atmosphere at around ambient temperature in the absence any monomer or solvent to produce peroxide or hydroperoxides linkages by gamma irradiation. Subsequently, the graft copolymerization is initiated by the free radicals produced from the thermal decomposition of peroxide or hydroperoxides linkages under heating with a benefit agent monomer in the appropriate solvent.

Two different situations arise, depending on whether peroxides or hydroperoxides are formed in the irradiated polymer. Either, the peroxidation leads to peroxidized polymer or else it leads to hydroperoxides.

Grafting may also be effected by means of chemical grafting, for example using ceric ions (A. Habeish et al, J. Appi. Polym.Sci. 1971, 15, 11–24) or using other conventional radical initiators such as potassium persulphate, e.g. per R. K. Samal, et al J. Polym. Mater. 1987, 4(3), 165–172.

There are also two general methods for preparing that class water-soluble or water dispersible material comprising a deposition aid having a polymeric backbone and a benefit agent grafted onto the backbone where the benefit agent includes or has attached thereto, group(s) which undergo the chemical change.

Method 3

First the deposition enhancement part is synthesised, or obtained commercially; and then the benefit agent(s) is/are grafted onto the backbone of the deposition enhancement part; and then the group(s) which undergo the chemical change are attached to the benefit agent.

Method 4

First the groups which undergo the chemical change are attached to the benefit agent. The resulting material is then grafted onto the polymeric backbone of the deposition enhancing part.

For Methods 3 and 4 the general method for preparing the deposition enhancing part if not commercially available may be achieved by a number of different synthetic routes, for example:

(a) polymerisation of suitable monomers, for example, enzymatic polymerisation of saccharides, e.g. per S. Shoda, & S. Kobayashi, Makromol. Symp. 1995, 99, 179–184 or oligosaccharide synthesis by orthogonal glycosylation e.g. per H. Paulsen, Angew. Chem. Int. Ed. Engl. 1995, 34, 1432–1434;

(b) derivatisation, hydrolysis, solvolysis, or other modification of a polymeric backbone which is either synthetic, or naturally occurring: especially polysaccharides, especially beta-1,4-linked polysaccharides, especially cellulose, mannan, glucomannan, galactomannan, xyloglucan.

(c) a combination of (a) and (b).

Some materials which are suitable as the deposition-enhancing part may be commercially available.

In addition, or alternatively, the degree of polymerisation of the backbone form (a), (b) or (c), or of a commercially available material, may be reduced or increased before, during, between, or after any of the steps (a), (b) or (c). The degree of polymerisation may be increased by further polymerisation or by cross linking agents.

For Methods 3 and 4 the general method for grafting the benefit agent (with group(s) attached in Method 4) onto the deposition enhancement part can be effected either:

by physical attraction between the delivery aid and the benefit agent, especially the use of a block copolymer where one block has a physical affinity for the benefit agent and the other block is the deposition aid; or by grafting the benefit agent onto the polymeric backbone of the delivery aid using a bond which is relatively hydrolytically stable. For example, one could use an ester bond which is more stable than the one intended to undergo the chemical change but which is not completely stable. For example a conjugated or aromatic ester. Such grafting can be accomplished by reacting the polymeric backbone with a benefit-agent reagent (especially acid halides, especially carboxylic acid halides, anhydrides, carboxylic acid anhydrides, carboxylic acids, isocyanates, triazine derivatives, amines, hydrazines) in a solvent which dissolves the backbone or delivery aid, swells the backbone or delivery aid, or does not swell the backbone or delivery enhancing part (depending on whether grafting the benefit agent first or last) but dissolves or swells the product.

For the grafting, typically, radiation methods may be used, as described above for Methods 1 and 2.

Compositions

The material according to the first aspect of the present invention may be incorporated into compositions containing only a diluent (which may comprise solid and/or liquid) and/or also comprising an active ingredient. The compound is typically included in said compositions at levels of from 0.01% to 25% by weight, preferably from 0.5% to 20%, most preferably from 1% to 15%.

The active ingredient in the compositions is preferably a surface active agent or a fabric conditioning agent. More than one active ingredient may be included. For some applications a mixture of active ingredients may be used.

The compositions of the invention may be in any physical form e.g. a solid such as a powder or granules, a tablet, a solid bar, a paste, gel or liquid, especially, an aqueous based liquid. In particular the compositions may be used in laundry compositions, especially in liquid, powder or tablet laundry composition.

The compositions of the present invention are preferably laundry compositions, especially main wash (fabric washing) compositions or rinse-added softening compositions. The main wash compositions may include a fabric softening agent and rinse-added fabric softening compositions may include surface-active compounds, particularly non-ionic surface-active compounds, if appropriate.

The detergent compositions of the invention may contain a surface-active compound (surfactant) which may be chosen from soap and non-soap anionic, cationic, non-ionic, amphoteric and zwitterionic surface-active compounds and mixtures thereof. Many suitable surface-active compounds are available and are fully described in the literature, for example, in "Surface-Active Agents and Detergents", Volumes I and II, by Schwartz, Perry and Berch.

The preferred detergent-active compounds that can be used are soaps and synthetic non-soap anionic and non-ionic compounds.

The compositions of the invention may contain linear alkylbenzene sulphonate, particularly linear alkylbenzene sulphonates having an alkyl chain length of $C_8$–$C_{15}$. It is preferred if the level of linear alkylbenzene sulphonate is from 0 wt % to 30 wt %, more preferably 1 wt % to 25 wt %, most preferably from 2 wt % to 15 wt %.

The compositions of the invention may contain other anionic surfactants in amounts additional to the percentages quoted above. Suitable anionic surfactants are well-known to those skilled in the art. Examples include primary and secondary alkyl sulphates, particularly $C_8$–$C_{15}$ primary alkyl sulphates; alkyl ether sulphates; olefin sulphonates; alkyl xylene sulphonates; dialkyl sulphosuccinates; and fatty acid ester sulphonates. Sodium salts are generally preferred.

The compositions of the invention may also contain non-ionic surfactant. Nonionic surfactants that may be used include the primary and secondary alcohol ethoxylates, especially the $C_8$–$C_{20}$ aliphatic alcohols ethoxylated with an average of from 1 to 20 moles of ethylene oxide per mole of alcohol, and more especially the $C_{10}$–$C_{15}$ primary and secondary aliphatic alcohols ethoxylated with an average of from 1 to 10 moles of ethylene oxide per mole of alcohol. Non-ethoxylated nonionic surfactants include alkylpolyglycosides, glycerol monoethers, and polyhydroxyamides (glucamide).

It is preferred if the level of non-ionic surfactant is from 0 wt % to 30 wt %, preferably from 1 wt % to 25 wt %, most preferably from 2 wt % to 15 wt %.

Any conventional fabric conditioning agent may be used in the compositions of the present invention. The conditioning agents may be cationic or non-ionic. If the fabric conditioning compound is to be employed in a main wash detergent composition the compound will typically be non-ionic. For use in the rinse phase, typically they will be nonionic. They may for example be used in amounts from 0.5% to 35%, preferably from 1% to 30% more preferably from 3% to 25% by weight of the composition.

Suitable fabric conditioning agents are typically any of the free compounds corresponding to examples of the materials hereinbefore described as possible fabric conditioning benefit agent groups.

The compositions of the invention, when used as main wash fabric washing compositions, will generally also contain one or more detergency builders. The total amount of detergency builder in the compositions will typically range from 5 to 80 wt %, preferably from 10 to 60 wt %.

It is also possible to include certain mono-alkyl cationic surfactants which can be used in main-wash compositions for fabrics. Cationic surfactants that may be used include quaternary ammonium salts of the general formula $R_1R_2R_3R_4N^+$ $X^-$ wherein the R groups are long or short hydrocarbon chains, typically alkyl, hydroxyalkyl or ethoxylated alkyl groups, and X is a counter-ion (for example, compounds in which $R_1$ is a $C_8$–$C_{22}$ alkyl group, preferably a $C_8$–$C_{14}$ or $C_{12}$–$C_{14}$ alkyl group, $R_2$ is a methyl group, and $R_3$ and $R_4$, which may be the same or different, are methyl or hydroxyethyl groups); and cationic esters (for example, choline esters).

The choice of surface-active compound (surfactant), and the amount present, will depend on the intended use of the detergent composition. In fabric washing compositions, different surfactant systems may be chosen, as is well known to the skilled formulator, for handwashing products and for products intended for use in different types of washing machine.

The total amount of surfactant present will also depend on the intended end use and may be as high as 60 wt %, for example, in a composition for washing fabrics by hand. In compositions for machine washing of fabrics, an amount of from 5 to 40 wt % is generally appropriate. Typically the compositions will comprise at least 2 wt % surfactant e.g. 2–60%, preferably 15–40% most preferably 25–35%.

Detergent compositions suitable for use in most automatic fabric washing machines generally contain anionic non-soap surfactant, or non-ionic surfactant, or combinations of the two in any suitable ratio, optionally together with soap.

The compositions of the invention, when used as main wash fabric washing compositions, will generally also contain one or more detergency builders. The total amount of detergency builder in the compositions will typically range from 5 to 80 wt %, preferably from 10 to 60 wt %.

Inorganic builders that may be present include sodium carbonate, if desired in combination with a crystallisation seed for calcium carbonate, as disclosed in GB 1 437 950 (Unilever); crystalline and amorphous aluminosilicates, for example, zeolites as disclosed in GB 1 473 201 (Henkel), amorphous aluminosilicates as disclosed in GB 1 473 202 (Henkel) and mixed crystalline/amorphous aluminosilicates as disclosed in GB 1 470 250 (Procter & Gamble); and layered silicates as disclosed in EP 164 514B (Hoechst). Inorganic phosphate builders, for example, sodium orthophosphate, pyrophosphate and tripolyphosphate are also suitable for use with this invention.

The compositions of the invention preferably contain an alkali metal, preferably sodium, aluminosilicate builder. Sodium aluminosilicates may generally be incorporated in amounts of from 10 to 70% by weight (anhydrous basis), preferably from 25 to 50 wt %.

The alkali metal aluminosilicate may be either crystalline or amorphous or mixtures thereof, having the general formula: 0.8–1.5 Na$_2$O. Al$_2$O$_3$. 0.8–6 SiO$_2$ These materials contain some bound water and are required to have a calcium ion exchange capacity of at least 50 mg CaO/g. The preferred sodium aluminosilicates contain 1.5–3.5 SiO$_2$ units (in the formula above). Both the amorphous and the crystalline materials can be prepared readily by reaction between sodium silicate and sodium aluminate, as amply described in the literature. Suitable crystalline sodium aluminosilicate ion-exchange detergency builders are described, for example, in GB 1 429 143 (Procter & Gamble). The preferred sodium aluminosilicates of this type are the well-known commercially available zeolites A and X, and mixtures thereof.

The zeolite may be the commercially available zeolite 4A now widely used in laundry detergent powders. However, according to a preferred embodiment of the invention, the zeolite builder incorporated in the compositions of the invention is maximum aluminium zeolite P (zeolite MAP) as described and claimed in EP 384 070A (Unilever). Zeolite MAP is defined as an alkali metal aluminosilicate of the zeolite P type having a silicon to aluminium ratio not exceeding 1.33, preferably within the range of from 0.90 to 1.33, and more preferably within the range of from 0.90 to 1.20.

Especially preferred is zeolite MAP having a silicon to aluminium ratio not exceeding 1.07, more preferably about 1.00. The calcium binding capacity of zeolite MAP is generally at least 150 mg CaO per g of anhydrous material.

Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di and trisuccinates, carboxymethyloxy succinates, carboxymethyloxymalonates, dipicolinates, hydroxyethyliminodiacetates, alkyl- and alkenylmalonates and succinates; and sulphonated fatty acid salts. This list is not intended to be exhaustive.

Especially preferred organic builders are citrates, suitably used in amounts of from 5 to 30 wt %, preferably from 10 to 25 wt %; and acrylic polymers, more especially acrylic/maleic copolymers, suitably used in amounts of from 0.5 to 15 wt %, preferably from 1 to 10 wt %.

Builders, both inorganic and organic, are preferably present in alkali metal salt, especially sodium salt, form.

Compositions according to the invention may also suitably contain a bleach system. Fabric washing compositions may desirably contain peroxy bleach compounds, for example, inorganic persalts or organic peroxyacids, capable of yielding hydrogen peroxide in aqueous solution.

Suitable peroxy bleach compounds include organic peroxides such as urea peroxide, and inorganic persalts such as the alkali metal perborates, percarbonates, perphosphates, persilicates and persulphates. Preferred inorganic persalts are sodium perborate monohydrate and tetrahydrate, and sodium percarbonate.

Especially preferred is sodium percarbonate having a protective coating against destabilisation by moisture. Sodium percarbonate having a protective coating comprising sodium metaborate and sodium silicate is disclosed in GB 2 123 044B (Kao).

The peroxy bleach compound is suitably present in an amount of from 0.1 to 35 wt %, preferably from 0.5 to 25 wt %. The peroxy bleach compound may be used in conjunction with a bleach activator (bleach precursor) to improve bleaching action at low wash temperatures. The bleach precursor is suitably present in an amount of from 0.1 to 8 wt %, preferably from 0.5 to 5 wt %.

Preferred bleach precursors are peroxycarboxylic acid precursors, more especially peracetic acid precursors and pernoanoic acid precursors. Especially preferred bleach precursors suitable for use in the present invention are N,N,N', N',-tetracetyl ethylenediamine (TAED) and sodium noanoyloxybenzene sulphonate (SNOBS). The novel quaternary ammonium and phosphonium bleach precursors disclosed in U.S. Pat. No. 4,751,015 and U.S. Pat. No. 4,818,426 (Lever Brothers Company) and EP 402 971A (Unilever), and the cationic bleach precursors disclosed in EP 284 292A and EP 303 520A (Kao) are also of interest.

The bleach system can be either supplemented with or replaced by a peroxyacid. examples of such peracids can be found in U.S. Pat. Nos. 4,686,063 and 5,397,501 (Unilever). A preferred example is the imido peroxycarboxylic class of peracids described in EP A 325 288, EP A 349 940, DE 382 3172 and EP 325 289. A particularly preferred example is phtalimido peroxy caproic acid (PAP). Such peracids are suitably present at 0.1–12%, preferably 0.5–10%.

A bleach stabiliser (transition metal sequestrant) may also be present. Suitable bleach stabilisers include ethylenediamine tetra-acetate (EDTA), the polyphosphonates such as Dequest (Trade Mark) and non-phosphate stabilisers such as EDDS (ethylene diamine di-succinic acid). These bleach stabilisers are also useful for stain removal especially in products containing low levels of bleaching species or no bleaching species.

An especially preferred bleach system comprises a peroxy bleach compound (preferably sodium percarbonate optionally together with a bleach activator), and a transition metal bleach catalyst as described and claimed in EP 458 397A, EP 458 398A and EP 509 787A (Unilever).

The compositions according to the invention may also contain one or more enzyme(s). Suitable enzymes include the proteases, amylases, cellulases, oxidases, peroxidases and lipases usable for incorporation in detergent compositions. Preferred proteolytic enzymes (proteases) are, catalytically active protein materials which degrade or alter Protein types of stains when present as in fabric stains in a hydrolysis reaction. They may be of any suitable origin, such as vegetable, animal, bacterial or yeast origin.

Proteolytic enzymes or proteases of various qualities and origins and having activity in various pH ranges of from 4–12 are available and can be used in the instant invention. Examples of suitable proteolytic enzymes are the subtilins which are obtained from particular strains of *B. Subtilis B. licheniformis*, such as the commercially available subtilisins Maxatase (Trade Mark), as supplied by Gist Brocades N. V., Delift, Holland, and Alcalase (Trade Mark), as supplied by Novo Industri A/S, Copenhagen, Denmark.

Particularly suitable is a protease obtained from a strain of Bacillus having maximum activity throughout the pH range of 8–12, being commercially available, e.g. from Novo Industri A/S under the registered trade-names Esperase (Trade Mark) and Savinase (Trade-Mark). The preparation of these and analogous enzymes is described in GB 1 243 785. Other commercial proteases are Kazusase (Trade Mark obtainable from Showa-Denko of Japan), Optimase (Trade Mark from Miles Kali-Chemie, Hannover, West Germany), and Superase (Trade Mark obtainable from Pfizer of U.S.A.). Detergency enzymes are commonly employed in granular form in amounts of from about 0.1 to about 3.0 wt %. However, any suitable physical form of enzyme may be used.

The compositions of the invention may contain alkali metal, preferably sodium carbonate, in order to increase detergency and ease processing. Sodium carbonate may suitably be present in amounts ranging from 1 to 60 wt %, preferably from 2 to 40 wt %. However, compositions containing little or no sodium carbonate are also within the scope of the invention.

Powder flow may be improved by the incorporation of a small amount of a powder structurant, for example, a fatty acid (or fatty acid soap), a sugar, an acrylate or acrylate/maleate copolymer, or sodium silicate. One preferred powder structurant is fatty acid soap, suitably present in an amount of from 1 to 5 wt %.

Other materials that may be present in detergent compositions of the invention include sodium silicate; antiredeposition agents such as cellulosic polymers; soil release polymers; inorganic salts such as sodium sulphate; lather control agents or lather boosters as appropriate; proteolytic and lipolytic enzymes; dyes; coloured speckles; perfumes; foam controllers, fluorescers and decoupling polymers. This list is not intended to be exhaustive. However, many of these ingredients will be better delivered as benefit agent groups in materials according to the first aspect of the invention.

The detergent composition when diluted in the wash liquor (during a typical wash cycle) will typically give a pH of the wash liquor from 7 to 10.5 for a main wash detergent.

Particulate detergent compositions are suitably prepared by spray-drying a slurry of compatible heat-insensitive ingredients, and then spraying on or post-dosing those ingredients unsuitable for processing via the slurry. The skilled detergent formulator will have no difficulty in deciding which ingredients should be included in the slurry and which should not.

Particulate detergent compositions of the invention preferably have a bulk density of at least 400 g/l, more preferably at least 500 g/l. Especially preferred compositions have bulk densities of at least 650 g/liter, more preferably at least 700 g/liter.

Such powders may be prepared either by post-tower densification of spray-dried powder, or by wholly non-tower methods such as dry mixing and granulation; in both cases a high-speed mixer/granulator may advantageously be used. Processes using high-speed mixer/granulators are disclosed, for example, in EP 340 013A, EP 367 339A, EP 390 251A and EP 420 317A (Unilever).

Liquid detergent compositions can be prepared by admixing the essential and optional ingredients thereof in any desired order to provide compositions containing components in the requisite concentrations. Liquid compositions according to the present invention can also be in compact form which means it will contain a lower level of water compared to a conventional liquid detergent.

Substrate

The substrate may be any substrate onto which it is desirable to deposit benefit agents and which is subjected to treatment such as a washing or rinsing process.

In particular, the substrate may be fabric or of a personal nature such as hair, skin, teeth or nails, or of a domestic nature such as dishes, ceramics, metal, plastics or upholstery.

It has been found that particular good results are achieved when using a natural fabric substrate such as cotton, or fabric blends containing cotton.

Treatment

The treatment of the substrate with the material of the invention can be made by any suitable method such as washing, soaking or rinsing of the substrate.

Typically the treatment will involve a washing or rinsing method such as treatment in the main wash or rinse cycle of a washing machine and involves contacting the substrate with an aqueous medium comprising the material of the invention. Alternatively for personal care applications the treatment could be achieved, for example, by personal washing, bathing or showering.

The present invention will now be explained in more detail by reference to the following non-limiting examples:

EXAMPLE 1

Preparation of Cellulose Acetate 4-Methoxycinnamate

In the example, the delivery enhancing part is cellulose monoacetate. When the acetate groups hydrolyse off during the wash the affinity of the cellulose backbone for the cotton surface will increase. 4-methoxycinnamate is the benefit agent. It is a UV absorber which reduces photofading of dyes on fabric. The ester bond between the cellulose and the 4-methoxy cinnamate is relatively hydrolytically stable because of the conjugated unsaturation.

A mixture of 123 mg 4-methoxycinnamoyl chloride, 100 mg of N,N-dimethyl-4-aminopyridine, 1 ml of pyridine, and a solution of 2.0 g of water-soluble cellulose acetate (DS~0.5) in 40 ml of 1-methyl-2-pyrrolidone solvent, were stirred together at 50° C. for 3 hours. Most of the solvent was removed under vacuum to leave a very viscous solution. When this solution was poured into water a clear solution was obtained. This experiment demonstrates how a normally water-insoluble benefit agent can be dissolved in water. It also demonstrates the grafting of the benefit agent onto the synthesised delivery aid (cellulose acetate).

The aqueous solution was poured into an excess of acetone to precipitate the polymer. The precipitated polymer was filtered off and dried.

EXAMPLE 2

Preparation of Cellulose 2-(2-Hydroxy-1-Oxopropoxy)Propanoate 4-Methoxycinnamate Cellulose 2-(2-hydroxy-1-oxopropoxy)propanoate is the delivery enhancing part. When the 2-(2-hydroxy-1-oxopropoxy)propanoate groups hydrolyse-off during the wash the affinity of the cellulose backbone for the cotton surface will increase. 4-methoxycinnamate is a benefit agent, as in Example 1.

A mixture of 130 mg 4-methoxycinnamoyl chloride and 29.7 g of cellulose solution (obtained by dissolving 14 g of microcrystalline cellulose (Avicel PH105) swollen with 14 g of N,N-dimethylacetamide into a mixture of 200 ml of N,N-dimethylacetamide and 16.8 g of lithium chloride) was treated with 1.5 ml of triethyl amine and stirred at 75° C. for 1.5 hours.

Then (following DE 3,322,118 for preparation of cellulose 2-(2-hydroxy-1-oxopropoxy)propanoate) 2.33 g lactide (3,6-dimethyl-1,4-dioxane-2,5-dione) was added to the mixture and stirred at 75° C. for 1.5 hours.

Cellulose 2-(2-hydroxy-1-oxopropoxy)propanoate 4-methoxycinnamate was isolated by ipetting the reaction mixture into 300 ml of methanol. The product gel was washed ith a further two batches of 300 ml of methanol.

The cellulose 2-(2-hydroxy-1-oxopropoxy)propanoate was dried under vacuum at room temperature.

EXAMPLE 3

Preparation of Cellulose Acetate Grafted With Methylmethacrvlate (MMA) by Mutual Irradiation In this Example, the benefit agent is MAA, which is a crease-resist agent.

Cellulose acetate (CA) was immersed in a mixture which contains, MAA, water and a single additional liquid at room temperature for 24 hr; subsequently the reaction mixture was flushed with oxygen-free nitrogen for 20 minutes, then the reaction bottle was tightly sealed, the reaction were carried out at a 9000 Ci $^{60}$Co γ-source at room temperature. After a given irradiation dose (the dose rate was determined by Fricke dosimetry), the solutions were filtered, the copolymeric products of MAA grafting on CA were immersed in an excess of methanol for at least 24 hr., then filtered to remove PMAA and unreaction monomer MAA.

Subsequently the grafted CA was washed with large amount of methanol again, to remove homopolymer (PMAA) and unreacted monomer (MAA) thoroughly. After this step the methanol was evaporated off in fume cupboard and the grafted CA was dried to constant mass at 60° C. in an oven and finally dried in a vacuum at 45° C. Thereafter, the combined methanolic solutions of PMAA and MAA were evaporated in a fume cupboard. The residue was dried in an oven at 80° C. Subsequently the dry mixture of PMAA and MAA was swollen and thoroughly washed with acetone to remove unreacted monomer. The pure PMAA was isolated by evaporation in a fume cupboard, and dried to constant weight in an 80° C. oven and final drying in a vacuum oven at 45° C. The amount of grafted monomer was taken as the increase in weight after solvent-extraction of homopolymer and drying. The percent grafting is defined as the ratio of the increase in weight to the initial polymeric (CA) weight as follows:

Grafting $(GD)\ \%=100\times(W_F-W_I)/W_I$ where $W_F$=Final grafting copolymeric weight; $W_I$=Initial polymeric weight;

The percent of homopolymer is defined as the ratio of the homopolymer weight to the initial monomer weight as follows:

% Homopolymer $(HP)=100\times$(Wt. of PMAA/Wt. of initial MAA).

The total conversion and grafting efficiency were calculated as follows

% Total conversition $(TC)=100\times$[Wt. of PMAA+$(W_F-W_I)$]/(Wt. of initial MAA).

where $W_F$=Final grafting polymeric weight; $W_I$=Initial polymeric weight

% Grafting efficiency $(GE)=100\times$[Wt. of PMAA in grafting/Total Wt. of PMAA formed]

EXAMPLE 4

Preparation of Graft Cellulose Acetate by Polymer Peroxide or Hydroperoxides Initiated Methods In an alternative method using pure CA, the latter was directly exposed in γ-source under air atmosphere at room temperature. Pre-irradiated CA was swollen in MAA and in a single or mixture of liquids. Then, graft copolymerization was carried out in water bath at 60° C. under pure nitrogen atmosphere for 6 hr.

After reaction, the mixtures were filtered and the copolymeric products of MAA grafted onto the CAA were immersed in an excess of methanol at least 24 hr., then filtered again. Subsequently, the grafted CA was washed with a large amount of methanol again to remove homopolymer (PMAA) and unreacted monomer (MAA) thoroughly. Afterwards, they were dried to constant weight in a vacuum oven at 45° C. Thereafter, the liquid which was obtained after removing PMAA and MAA, was collected and evaporated in a fume cupboard and dried at 80° C. in an oven. Subsequently, the mixture of PMAA and MAA was swollen and thoroughly washed with acetone to remove unreacted monomer and the pure PMAA was dried to constant weight in a vacuum oven at 45°C. The grafting rate was calculated.

By analysis, in each of Examples 1–4, the average degree of substituion of hydrolysable groups was found to be between 0.1 to 3.

Examples 5–16 are formulation Examples. In each case, the "Polymer" specified is the material of Example 1.

EXAMPLE 5

Spray-Dried Powder

| Component | % w/w |
|---|---|
| Na PAS | 11.5 |
| Dobanol 25-7 | 6.3 |
| Soap | 2.0 |
| Zeolite | 24.1 |
| SCMC | 0.6 |
| Na Citrate | 10.6 |
| Na Carbonate | 23.0 |
| Polymer | 4.0 |
| Silicone Oil | 0.5 |
| Dequest 2066 | 0.4 |
| Sokalan CP5 | 0.9 |
| Savinase 16L | 0.7 |
| Lipolase | 0.1 |
| Perfume | 0.4 |
| Water/salts | to 100 |

EXAMPLE 6

Detergent Granulate Prepared by Non-Spray Drying Method

The following composition was prepared by the two-stage mechanical granulation method described in EP-A-367 339.

| Component | % w/w |
|---|---|
| NaPAS | 13.5 |
| Dobanol 25-7 | 2.5 |
| STPP | 45.3 |
| Na Carbonate | 4.0 |
| Polymer | 3.8 |
| Na Silicate | 10.1 |
| Minors | 1.5 |
| Water | balance |

EXAMPLE 7

Isotropic Laundry Liquid

| Component | % w/w |
|---|---|
| Na-citrate (37.5%) | 10.7 |
| Propyleneglycol | 7.5 |
| Ethylene Glycol | 4.5 |
| Borax | 3.0 |
| Savinase 16L | 0.3 |
| Lipolase | 0.1 |
| Polymer | 3.5 |
| Monoethanolamine | 0.5 |
| Cocofatty acid | 1.7 |
| NaOH (50%) | 2.2 |
| LAS | 10.3 |
| Dobanol 25-7 | 6.3 |
| LES | 7.6 |
| Minors | 1.3 |
| (adjust pH to 7 with NaOH) | |
| Water | up to 100 |

EXAMPLE 8

Structured Laundry Liquid

| Component | % w/w |
|---|---|
| LAS | 16.5 |
| Dobanol 25-7 | 9 |
| Oleic acid (Priolene 6907) | 4.5 |
| Zeolite | 15 |
| KOH, neutralisation of acids and pH to 8.5 | |
| Citric acid | 8.2 |
| deflocculating polymer | 1 |

| Component | % w/w |
|---|---|
| Protease | 0.38 |
| Lipolase | 0.2 |
| Polymer | 2.0 |
| Minors | 0.4 |
| Water | to 100% |

| Component | % w/w |||||||||
|---|---|---|---|---|---|---|---|---|
| | Ex. 9 | Ex. 10 | Ex. 11 | Ex. 12 | Ex. 13 | Ex. 14 | Ex. 15 | Ex. 16 |
| Na alcohol EO sulphate | 0.0 | 0.0 | 0.0 | 0.0 | 0.0 | 0.0 | 0.0 | 13.3 |
| linear alkylbenzenesulfonate, Na salt (LAS) | 5.1 | 5.9 | 5.8 | 7.3 | 8.2 | 9.9 | 23.7 | 7.6 |
| sodium stearate | 0.0 | 0.3 | 0.3 | 0.3 | 1.0 | 1.2 | 0.0 | 0.0 |
| fatty acid | 1.7 | 0.3 | 0.3 | 0.4 | 0.0 | 0.0 | 0.0 | 0.0 |
| alcohol ethoxylate 9EO | 0.0 | 0.0 | 0.0 | 0.0 | 0.0 | 0.0 | 0.0 | 7.6 |
| alcohol ethoxylate 7EO branched | 2.5 | 3.9 | 3.9 | 4.8 | 4.3 | 5.2 | 0.0 | 0.0 |
| alcohol ethoxylate 3EO branched | 3.4 | 2.9 | 2.9 | 3.6 | 2.3 | 2.8 | 0.0 | 0.0 |
| sodium citrate | 0.0 | 0.0 | 0.0 | 0.0 | 3.3 | 7.4 | 0.0 | 4.8 |
| propylene glycol | 0.0 | 0.0 | 0.0 | 0.0 | 0.0 | 0.0 | 0.0 | 6.4 |
| sorbitol | 0.0 | 0.0 | 0.0 | 0.0 | 0.0 | 0.0 | 0.0 | 4.3 |
| sodium borate | 0.0 | 0.0 | 0.0 | 0.0 | 0.0 | 0.0 | 0.0 | 2.9 |
| sodium silicate | 0.4 | 5.9 | 5.8 | 7.3 | 1.5 | 0.0 | 7.9 | 0.0 |
| sodium carbonate | 17.6 | 9.0 | 12.0 | 12.4 | 9.2 | 17.5 | 17.3 | 0.0 |
| sodium bicarbonate | 0.0 | 0.0 | 0.0 | 6.1 | 0.9 | 3.8 | 0.0 | 0.0 |
| sodium sulphate | 19.8 | 16.2 | 13.9 | 16.3 | 0.0 | 0.0 | 26.1 | 0.0 |
| STPP | 0.0 | 22.1 | 22.1 | 27.4 | 0.0 | 0.0 | 14.3 | 0.0 |
| zeolite A24 (anhydrous) | 19.8 | 0.0 | 0.0 | 0.0 | 28.0 | 33.8 | 0.0 | 0.0 |
| sodium perborate tetrahydrate | 11.7 | 17.9 | 17.8 | 0.0 | 0.0 | 0.0 | 0.0 | 0.0 |
| coated percarbonate 13.5 avOx | 0.0 | 0.0 | 0.0 | 0.0 | 18.0 | 0.0 | 0.0 | 0.0 |
| TAED granule (83%) | 2.1 | 2.0 | 2.0 | 0.0 | 5.2 | 0.0 | 0.0 | 0.0 |
| minors | 5.9 | 3.8 | 3.2 | 4.2 | 8.0 | 8.3 | 0.8 | 1.2 |
| water | 0.0 | 0.0 | 0.0 | 0.0 | 0.0 | 0.0 | 0.0 | 46.9 |
| polymer | 10.0 | 10.0 | 10.0 | 10.0 | 10.0 | 10.0 | 10.0 | 5.0 |
| TOTAL: | 100.0 | 100.0 | 100.0 | 100.0 | 100.0 | 100.0 | 100.0 | 100.0 |

Raw Material Specification

| Component | Specification |
|---|---|
| LAS | Linear Alkyl Benzene Sulphonic-acid, Marlon AS3, ex Huls |
| Na-LAS | LAS-acid neutralised with NaOH |
| Dobanol 25-7 | C12–15 ethoxylated alcohol, 7E0, ex Shell |
| LES | Lauryl Ether Sulphate, Dobanol 25-S3, ex Shell |
| Zeolite | Wessalith P, ex Degussa |
| STPP | Sodium Tri PolyPhosphate, Thermphos NW, ex Hoechst |
| Dequest 2066 | Metal chelating agent, ex Monsanto |
| Silicone oil | Antifoam, DB 100, ex Dow Corning |
| Tinopal CBS-X | Fluorescer, ex Ciba-Geigy |
| Lipolase | Type 100L, ex Novo |
| Savinase 16L | Protease, ex Novo |
| Sokalan CP5 | Acrylic/Meleic Builder Polymer ex BASF |
| Deflocculating Polymer | Polymer A-1-1 disclosed in EP-A-346 995 |
| SCMC | Sodium Carboxymethyl Cellulose |

What is claimed is:

1. A water-soluble or water dispersible compound for deposition onto a cellulosic substrate during a textile treatment process wherein the compound comprises:

(i) a deposition enhancing part having a beta 1,4 linked polysaccharide backbone composed of saccharide rings having a carboxylic acid esterified therewith; and (ii) a benefit agent attached to the deposition enhancing part by a covalent hydrolytically stable bond; said benefits agents being selected from softening agents, lubricants, sunscreens, fluorescers, dyes, perfumes, dye fixatives, crease resist or preventative agents, water repellent agents and ironing aids, such that the compound undergoes hydrolysis during the textile treatment process whereby cleavage of the carboxylic acid esters increases the affinity of the deposition enhancing part onto the cellulosic substrate.

2. The compound of claim 1, having the general formula (I):

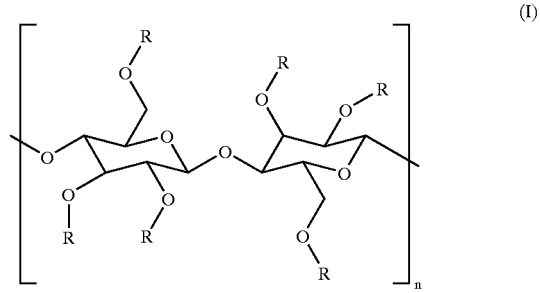

wherein at least one or more R groups of the Beta-1,4 linked polysaccharide polymer are independently selected benefit agent groups and further comprise at least one or more R groups independently selected from groups of formulae:

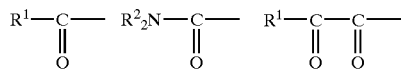

-continued

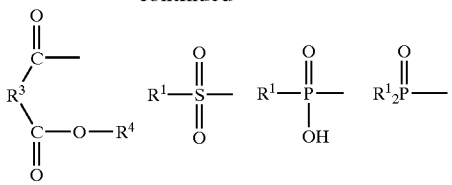

wherein each $R^1$ is independently selected from $C_{1-20}$ alkyl, $C_{2-20}$ alkenyl and $C_{5-7}$ aryl any of which is optionally substituted by one or more substituents independently selected from $C_{1-4}$ alkyl, $C_{1-12}$ alkoxy, hydroxyl, vinyl and phenyl groups;

each $R^2$ is independently selected from hydrogen and groups $R^1$ as hereinbefore defined;

$R^3$ is a bond or is selected from $C_{1-4}$ alkylene, $C_{2-4}$ alkenylene and $C_{5-7}$ arylene groups, the carbon atoms in any of these being optionally substituted by one or more substituents independently selected from $C_{1-12}$ alkoxy, vinyl, hydroxyl, halo and amine groups;

each $R^4$ is independently selected from hydrogen, counter cations such as alkali metal or ½ Ca of ½ Mg, and groups $R^1$ as hereinbefore defined;

n is selected so that the molecular weight of the polymer is in the range of 1,000 to 2,000,000; and groups R which together with the oxygen atom forming the linkage to the respective saccharide ring forms an ester or hemi-ester group of a tricarboxylic- or higher polycarboxylic- or other complex acid such as citric acid, an amino acid, a synthetic amino acid analogue or a protein.

3. The compound of claim 1, wherein the carboxylic acid ester group(s) is/are independently selected from one or more of acetate, propanoate, trifluroacetate, 2-(2-hydroxy-1-oxopropoxy) propanoate, lactate, glycolate, pyruvate, crotonate, isovalerate, cinnamate, formate, salicylate, carbamate, methylcarbamate, benzoate, gluconate, methanesulphonate, toluene sulphonate, groups and hemiester groups of fumaric, malonic, itaconic, oxalic, maleic, succinic, tartaric, aspartic, glutamic, and malic acids.

4. The compound of claim 1, wherein the average degree of substitution on the saccharide rings of the groups which undergo the chemical change is from 0.1 to 3.

5. The compound of claim 1, further comprising one or more pendant groups which are neither benefit agents nor groups which undergo a chemical change to enhance substrate affinity.

6. The compound of claim 5, wherein the number of the one or more pendant groups is up to 65% of the total number of groups pendant on the polymeric backbone.

7. A method of depositing a benefit agent onto a substrate, the method comprising:

(a) preparing a liquor comprising a water-soluble or water dispersible material for deposition onto a cellulosic substrate during a textile treatment process wherein the material comprises:

(i) a deposition enhancing part having a Beta 1,4 linked polysaccharide backbone having a carboxylic acid esterified therewith; and (ii) a benefit agent attached to the deposition enhancing part by a covalent hydrolytically stable bond; said benefit agents being selected from softening agents, lubricants, sunscreens, fluorescers, dyes, perfumes, dye fixatives, crease resist or preventative agents, water repellent agents and ironing aids, such that the compound undergoes hydrolysis during the textile treatment process, whereby cleavage of the carboxylic acid esters increases the affinity of the deposition enhancing part onto the cellulosic substrate; and (b) contacting said substrate with said liquor.

8. The method of claim 7, wherein the chemical change is catalysed by enzyme or another catalyst.

9. The method of claim 7, wherein the hydrolysis occurs in or to a group covalently bonded to or in the deposition enhancing part but not bonded to the benefit aid.

10. The method of claim 7, wherein the hydrolysis results in the modification or loss of one or more groups on the polysaccharide backbone of the deposition enhancing part.

11. The method of claim 10, wherein the groups are in a pendant position on the polysaccharide backbone.

12. The compound of claim 1 further comprising a surfactant.

13. The compound of claim 1 wherein the water-soluble or water-dispersible material is present in an amount from 0.01 to 25%.

* * * * *